(12) United States Patent
Tsai et al.

(10) Patent No.: US 7,688,439 B2
(45) Date of Patent: Mar. 30, 2010

(54) OPTICAL MEASURING SYSTEM

(75) Inventors: Shu-Hui Tsai, Hsinchu County (TW); Shiow-Harn Lee, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 315 days.

(21) Appl. No.: 11/776,544

(22) Filed: Jul. 11, 2007

(65) Prior Publication Data

US 2008/0024774 A1  Jan. 31, 2008

(30) Foreign Application Priority Data

Jul. 28, 2006   (TW) .............................. 95127672 A

(51) Int. Cl.
*G01N 1/10* (2006.01)
*G01B 9/08* (2006.01)

(52) U.S. Cl. ...................................... 356/246; 356/392
(58) Field of Classification Search .......... 356/244–248
See application file for complete search history.

(56) References Cited

U.S. PATENT DOCUMENTS

| | | | |
|---|---|---|---|
| 4,750,837 A | 6/1988 | Gifford et al. | |
| 4,802,768 A | 2/1989 | Gifford et al. | |
| 4,945,250 A | 7/1990 | Bowen et al. | |
| 4,956,148 A | 9/1990 | Grandone | |
| 4,977,325 A | 12/1990 | Bowen et al. | |
| 5,035,861 A | 7/1991 | Grandone | |
| 6,074,616 A | 6/2000 | Buechler et al. | |
| 6,084,680 A | 7/2000 | Tuunanen et al. | |
| 6,144,455 A | 11/2000 | Tuunanen et al. | |
| 6,194,222 B1 | 2/2001 | Buechler et al. | |
| 6,232,608 B1 | 5/2001 | Giebeler et al. | |
| 6,236,456 B1 | 5/2001 | Giebeler et al. | |
| 6,313,471 B1 | 11/2001 | Giebeler et al. | |
| 6,316,774 B1 | 11/2001 | Giebeler et al. | |
| 6,628,382 B2 | 9/2003 | Robertson | |
| 6,656,428 B1 | 12/2003 | Clark et al. | |
| 6,673,315 B2 * | 1/2004 | Sheridan et al. | ............... 422/50 |
| 6,809,826 B2 | 10/2004 | Robertson | |

(Continued)

FOREIGN PATENT DOCUMENTS

| | | |
|---|---|---|
| CN | 1221119 | 6/1999 |
| CN | 2452014 | 10/2001 |
| CN | 1423113 | 6/2003 |
| CN | 1427251 | 7/2003 |
| WO | 9100994 | 1/1991 |

(Continued)

OTHER PUBLICATIONS

"1st Office Action of China counterpart application", issued on Jun. 5, 2009, p. 1-p. 6.

*Primary Examiner*—Michael P Stafira
(74) *Attorney, Agent, or Firm*—Jianq Chyun IP Office

(57) ABSTRACT

An optical measuring system includes a carrying tray for carrying a specimen, a first light source module, a second light source module and an optical measuring module. The first light source module is disposed at the first side of the carrying tray and the specimen is disposed on the optical path of the first light source module. The second light source module is disposed at the second side of the carrying tray and the specimen is disposed on the optical path of the second light source module. The optical measuring module is disposed at the first side or the second side of the carrying tray, and the specimen is located within the probing range of the optical measuring module.

38 Claims, 14 Drawing Sheets

U.S. PATENT DOCUMENTS

| | | |
|---|---|---|
| 6,830,731 B1 | 12/2004 | Buechler et al. |
| 6,949,754 B2 * | 9/2005 | Peukert et al. ........... 250/458.1 |
| 2002/0127742 A1 | 9/2002 | Bunn et al. |
| 2008/0145040 A1 * | 6/2008 | Hunt .............................. 396/5 |
| 2008/0273205 A1 * | 11/2008 | Lee et al. .................... 356/440 |

FOREIGN PATENT DOCUMENTS

| | | |
|---|---|---|
| WO | 9100995 | 1/1991 |
| WO | 9214137 | 8/1992 |
| WO | 9711354 | 3/1997 |

* cited by examiner

OPTICAL MEASURING SYSTEM

CROSS-REFERENCE TO RELATED APPLICATION

This application claims the priority benefit of Taiwan application serial no. 95127672, filed Jul. 28, 2006. All disclosure of the Taiwan application is incorporated herein by reference.

BACKGROUND OF THE INVENTION

1. Field of the Invention

The present invention generally relates to an optical measuring system, and more particularly, to an optical measuring system suitable for conducting reflective optical measurement and transmittive-absorptive optical measurement on a same assay table.

2. Description of Related Art

The photoluminescence (PL) spectroscopic analysis is a powerful and non-destructive technique to test the optical characteristics of luminous semiconductor materials. Furthermore, many material parameters including doped impurity kinds, band-gap values, activation energy of impurity and the like can be revealed from an optical spectrum by analyzing the PL data, and the constituents of a compound can be estimated from peak energies of a luminescence spectrum.

In order to observe the portions without spontaneous fluorescence in biometric tissues, it is needed to add fluorescence dye. The fluorescence protein technique is a significant invention in fluorescence-adding field recently. Fluorescence protein has no biological toxicity and can be compiled in deoxyribose nucleic acid (DNA) of target cells so as to be exhibited. If fluorescence protein is compiled with other proteins, the exhibition intensity and occurring positions of specific proteins in cells can be tracked by means of fluorescence intensity. In an instrument of measuring fluorescence reactions, a light source and an optical detector are usually disposed at a same side of the instrument, where the fluorescence substance of specimen is stimulated by the light source so as to measure the fluorescence reaction of the specimen by using the optical detector. The above-mentioned optical measurement technique by disposing a light source and an optical detector at a same side of the specimen is termed as reflective measurement.

The light absorption analysis is also broadly applicable to testing various materials where some substances having specific absorption spectrums are utilized. By illuminating a specimen with light having a specific wavelength range, probing the optical spectrum of the specimen transmitted by the light and comparing the spectrum of incident light with the spectrum of the transmitted light, the absorption spectrum of the specimen can be revealed. In an instrument for measuring light absorption however, a light source and an optical detector are usually disposed at both sides of a specimen. By illuminating a specimen with the light source, the optical detector is able to measure the optical spectrum of the specimen transmitted by the light. The above-mentioned optical measurement technique by disposing a light source and an optical detector at different sides of the specimen is termed as transmittive-absorptive measurement.

Due to the application demands of nanometer materials and biochemical analytes today, where the samples have numerous kinds but small amount per batch for testing, and the novelty of the sample materials, in particular, in terms of the application of biochemical analyses, there are some biochemical ferments in addition to protein and DNA, therefore, to develop an optical testing system with high-sensitivity and high-dynamic range which is able to simultaneously obtain some results provided for evaluating material structure, components and quality thereof by conducting PL analyses and optical absorption analyses is one of vital measurement technique projects in advancing nanometer and biometric materials.

U.S. Pat. Nos. 6,074,616, 6,830,731B1 and 6,194,222B1 provide fluorescence optical testing methods with high-sensitivity and high-dynamic range, which target to conduct fluorescent marking with different contents on the fluorescent marking substance of specimen to suit biometric marking proteins with different contents. U.S. Pat. Nos. 6,628,382B2 and 6,809,826B2 provide a fluorescent radiation and optical absorption testing method, where the optical testing is conducted by using different assay tables.

Usually, a reflective measurement and a transmittive-absorptive measurement on a specimen are conducted by using different assay tables, respectively, that is, a single assay table is in charge of an optical measurement only. World Patent WO9,214,137 provides a device for measuring fluorescent radiation and optical absorption. However, the device is applicable to liquid specimen only, which limits the applications thereof and can not be used for testing diverse biometric material, such as biochip.

SUMMARY OF THE INVENTION

Accordingly, the present invention is directed to an optical measuring system suitable to conduct reflective optical measurement and transmittive optical measurement on a single assay table.

The present invention provides an optical measuring system, which includes a carrying tray for carrying specimen, a first light source module, a second light source module and a optical measuring module. The first light source module is disposed at the first side of the carrying tray and a specimen is located on the optical path of the first light source module. The second light source module is disposed at the second side of the carrying tray. The optical measuring module is disposed at the first side or the second side of the carrying tray, and the specimen is located within the probing range of the optical measuring module.

According to an embodiment of the present invention, the optical measuring system includes a carrying tray position servo unit connected to the carrying tray. By using the carrying tray position servo unit to adjust the position of the carrying tray, the specimen can be located within the probing range of the optical measuring module.

According to an embodiment of the present invention, the carrying tray of the optical measuring system includes a specimen-fixing mechanism for fixing the specimen onto the carrying tray. The specimen-fixing mechanism includes a carrying vessel, wherein the carrying vessel has a cavity for carrying specimen, or a plurality of cavities with different depths and different widths for carrying specimens of different sizes, and at least a hollow out cavity is disposed at the bottom of the above-mentioned cavity.

According to an embodiment of the present invention, the first light source module of the above-mentioned optical measuring system includes a first optical modulation unit for modulating the light emitted by the first light source module. The first optical modulation unit includes a modification sheet for intermittently blocking the optical path of the first light source module so as to enable the optical measuring system to perform high-sensitivity phase-locking optical measurement.

According to an embodiment of the present invention, the optical measuring system includes a position servo unit of first light source module for adjusting the distance between the first light source module and the carrying tray such that a specimen may be allocated on the optical path of the first light source module.

According to an embodiment of the present invention, the second light source module of the optical measuring system may emit a monochromatic light or a multi-chromatic light with different wavelengths. The second light source module includes a second optical modulation unit for modulating the light of the second light source module. The second optical modulation unit includes a modification sheet for intermittently blocking the optical path of the second light source module so as to enable the optical measuring system to perform high-sensitivity phase-locking optical measurement.

According to an embodiment of the present invention, the optical measuring system includes a position servo unit of second light source module for adjusting the distance between the second light source module and the carrying tray such that a specimen may be allocated on the optical path of the second light source module.

According to an embodiment of the present invention, the optical measuring module of the optical measuring system includes a carrying barrel which has a lens and a washer and the washer is for adjusting the position of the lens in the carrying barrel.

According to an embodiment of the present invention, the optical measuring system includes an optical measuring position servo unit for adjusting the distance between the optical measuring module and the carrying tray such that the specimen may be allocated within the probing range of the optical measuring module.

According to an embodiment of the present invention, the optical measuring module of the above-mentioned optical measuring system is disposed at the first side of the carrying tray, where the first light source module emits a light onto the specimen so that the optical measuring module may conduct a reflective optical measurement on the specimen, while the second light source module emits a light onto the specimen so that the optical measuring module may conduct a transitive optical measurement on the specimen.

According to an embodiment of the present invention, the optical measuring system includes a detection circuit electrically connected to the optical measuring module for detecting the measuring results of the optical measuring module. The detection circuit includes a logarithmic amplifier to enable the optical measuring system to conduct high-sensitivity and high-dynamic range optical measurement.

According to an embodiment of the present invention, the specimen includes a carrying sheet, wherein the carrying sheet is divided into a plurality of regions in which substance to be tested is disposed.

According to an embodiment of the present invention, the optical measuring module conducts photometry on each above-mentioned region and compares the results of all regions so that an average value of two regions with less coefficient of variation (CV) is chosen as the measurement value according to the comparison results.

According to an embodiment of the present invention, the regions are arranged along the longitudinal direction of the carrying sheet in the optical measuring system.

As described above, the optical measuring system comprises two light source modules to conduct both reflective optical measurement and transmittive optical measurement on a same assay table so that a user may conduct various measurements without transferring a specimen between different assay tables, which not only saves time, but also avoids wastage of materials.

In addition, a washer may be used to adjust the lens position of the optical measuring module, which not only enables the optical measuring module to be assembled by using commercially available and finished optical components but also saves assembly cost significantly.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
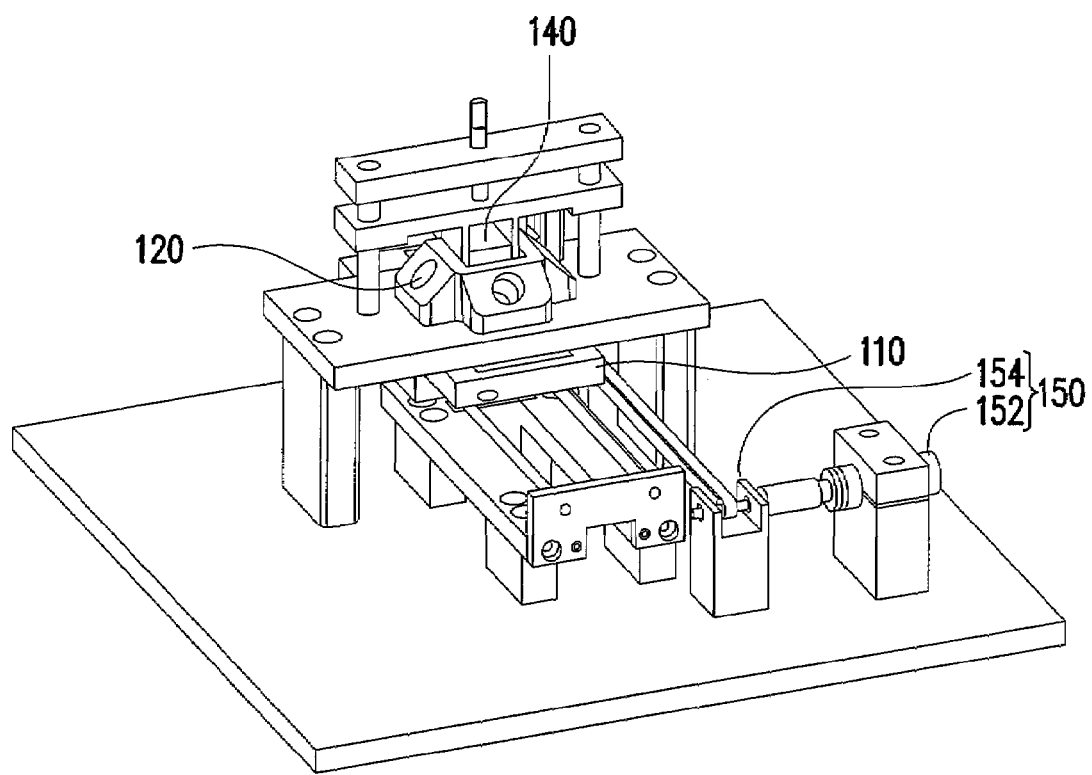
FIG. 1A is a 3-D schematic view of the optical measuring system according to an embodiment of the present invention.

Reference will now be made in detail to the present embodiments of the invention, examples of which are illustrated in the accompanying drawings. Wherever possible, the same reference numbers are used in the drawings and the description to refer to the same or like parts.

Figure 1B:
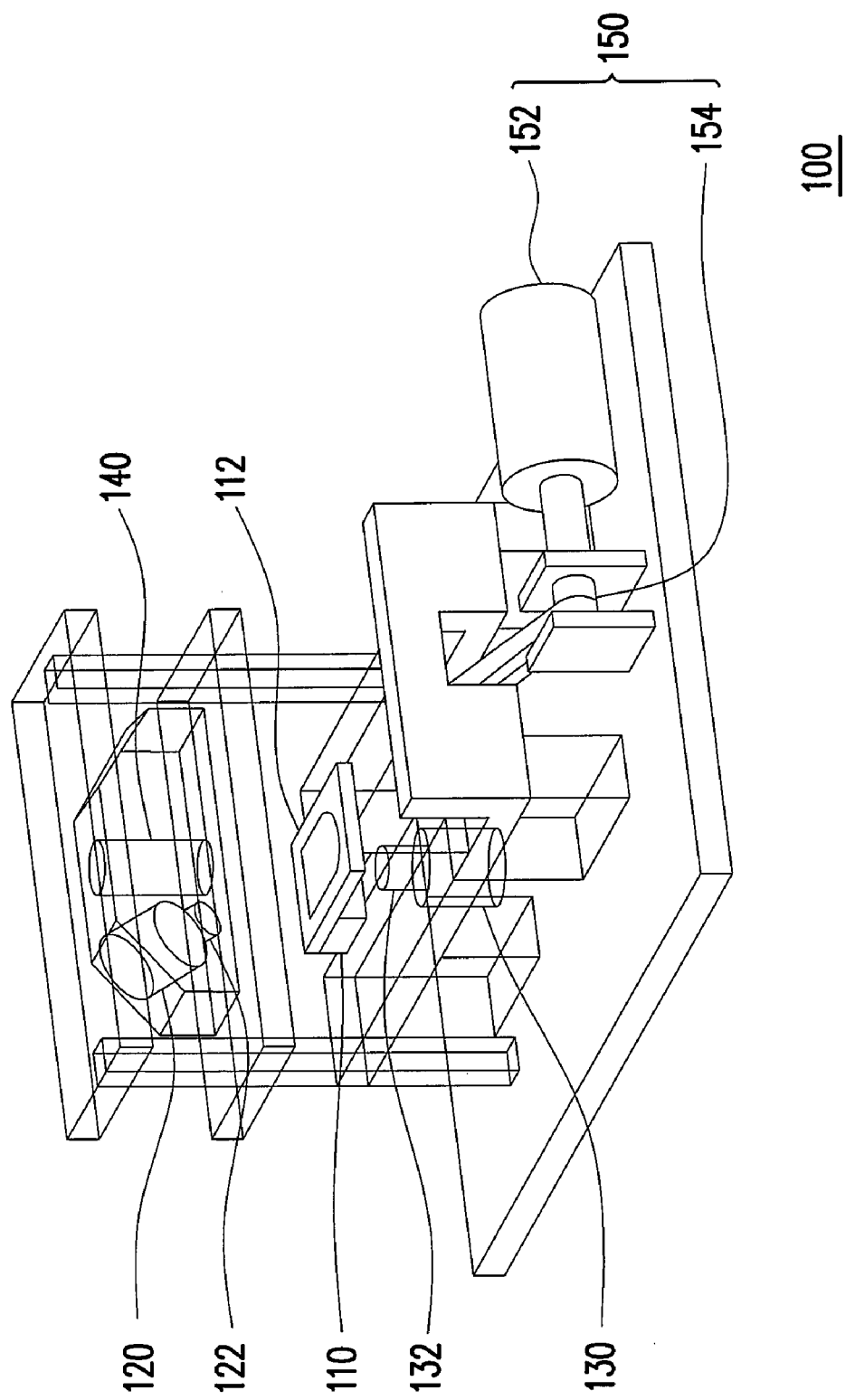
FIG. 1B is a wire-frame view of the optical measuring system according to another embodiment of the present invention.

FIG. 1A is a 3-D view of the optical measuring system according to an embodiment of the present invention, FIG. 1B is a wire-frame view of the optical measuring system according to another embodiment of the present invention. As the two embodiments are similar, thus a same component in FIGS. 1A and 1B is notated with a same symbol. Referring to FIGS. 1A and 1B, an optical measuring system 100 includes a carrying tray 110 for carrying specimen, a first light source module 120, a second light source module 130 and an optical measuring module 140.

The above-mentioned first light source module 120 and the optical measuring module 140 are located at the first side of the carrying tray 110, while the second light source module 130 is located at the second side of the carrying tray 110. Although in an embodiment of the present invention, the first side and the second side of the carrying tray 110 respectively mean the upper side and the lower side thereof, however so long as the two light source modules are respectively located at two sides of the carrying tray 110 to conduct a reflective optical measurement and a transmittive optical measurement on a same assay table, the design shall be construed to fall within the scope of the present invention. In an embodiment of the present invention, a specimen (not shown) is disposed at the first side of the carrying tray 110. However, one skilled in the art may dispose the specimen at the second side of the carrying tray 110. The specimen (not shown) includes optical fiber chip and flat biochip.

Figure 1C:
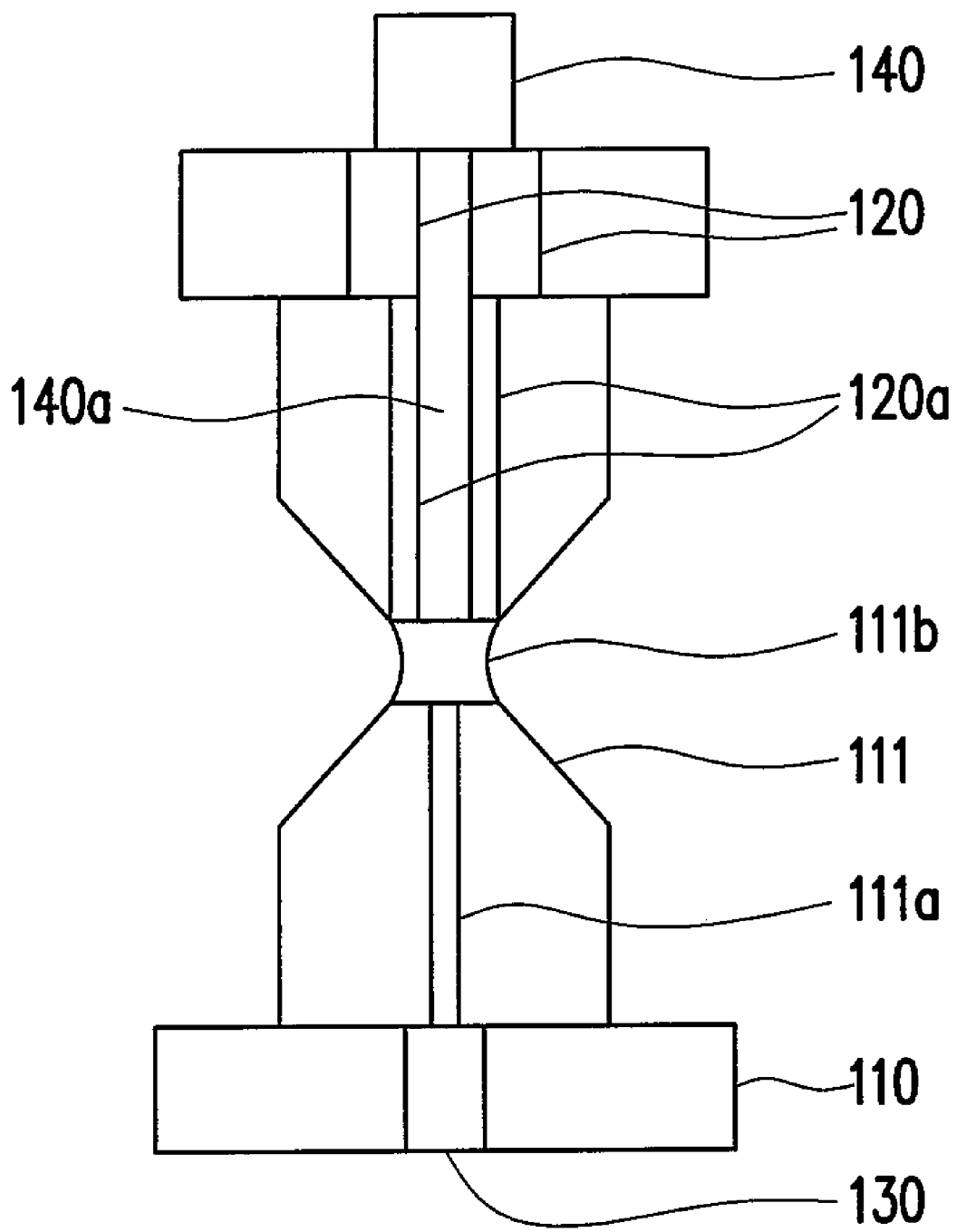
FIG. 1C is a schematic localized sectional drawing of the optical measuring system according to an embodiment of the present invention.

FIG. 1C is a schematic localized sectional view of the optical measuring system according to an embodiment of the present invention. Referring to FIG. 1C, in an optical fiber chip, a specimen is disposed on an optical fiber. The light emitted by the first light source module 120 is incident into specimen solution 111b via an optical fiber 120a, while the light emitted by the second light source module 130 is incident into specimen solution 111b via an optical fiber 111a. The optical measuring module 140 measures the transmitted light from the specimen solution 111b or the transmitted light from the specimen solution 111b through an optical fiber 140a.

Figure 1D:
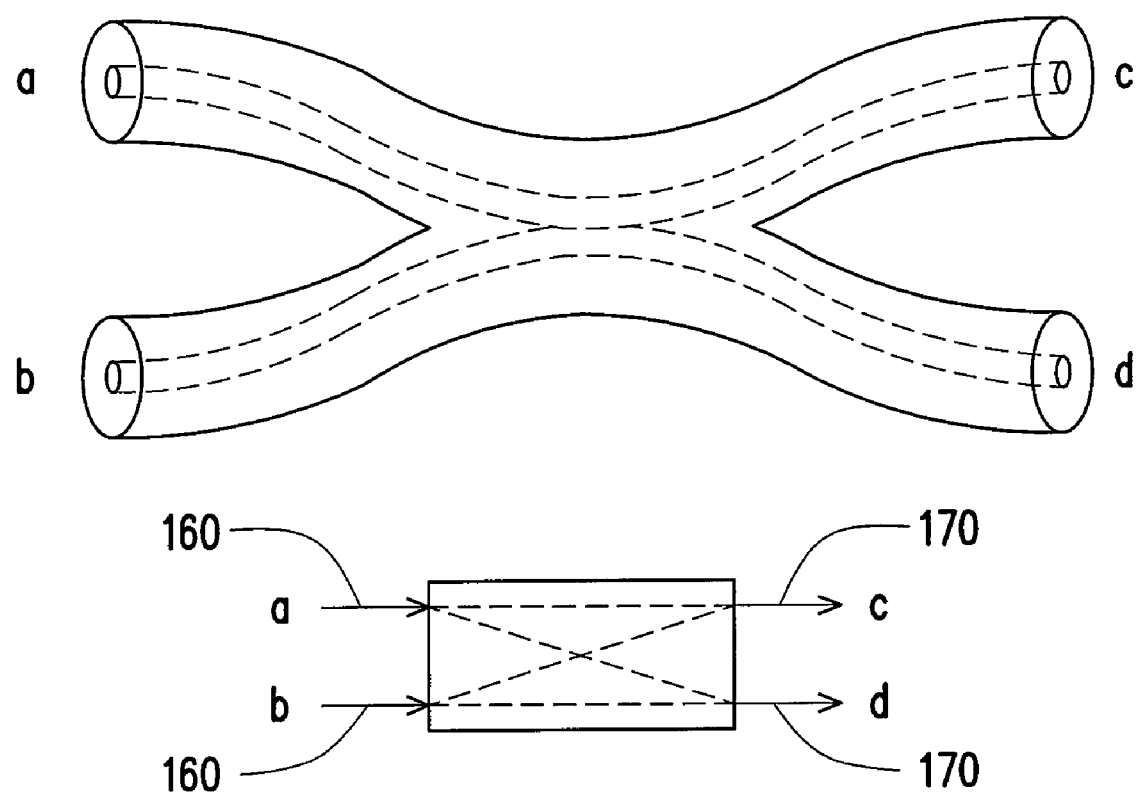
FIG. 1D is a view of an optical coupler.

FIG. 1D is a view of an optical coupler according to an embodiment of the present invention. Referring to FIG. 1D, an optical coupler may be used to place the specimen solution (not shown) at a position a or a position b. If a light 160 irradiates the specimen solution at the position a or the position b, the coupled signal of reaction light 170 can be measured respectively at a position c and a position d, wherein the coupling amount can be selected according to the required sensitivity.

In an embodiment of the present invention, the first light source module 120 and second light source module 130 provide a light with a single wavelength. However, those skilled in the art may modify the design using multiple light sources providing different wavelengths. The wavelengths provided by the first light source module 120 and second light source module 130 can be same or different.

The first light source module 120 further includes a first optical modulation unit 122 for modulating the light emitted by the first light source module 120. In an embodiment of the present invention, the first optical modulation unit 122 employs a modification sheet for intermittently blocking the optical path of the first light source module 120 so as to enable the optical measuring system 100 to perform high-sensitivity phase-locking optical measurement. Anyone skilled in the art may also employ any other schemes to conduct the modulation.

The second light source module 130 further includes a second optical modulation unit 132 for modulating the light emitted by the second light source module 130. In an embodiment of the present invention, the second optical modulation unit 132 employs a modification sheet for intermittently blocking the optical path of the second light source module 130 so as to enable the optical measuring system 100 to perform high-sensitivity phase-locking optical measurement. Anyone skilled in the art may also employ any other schemes to conduct the modulation.

Figure 5:
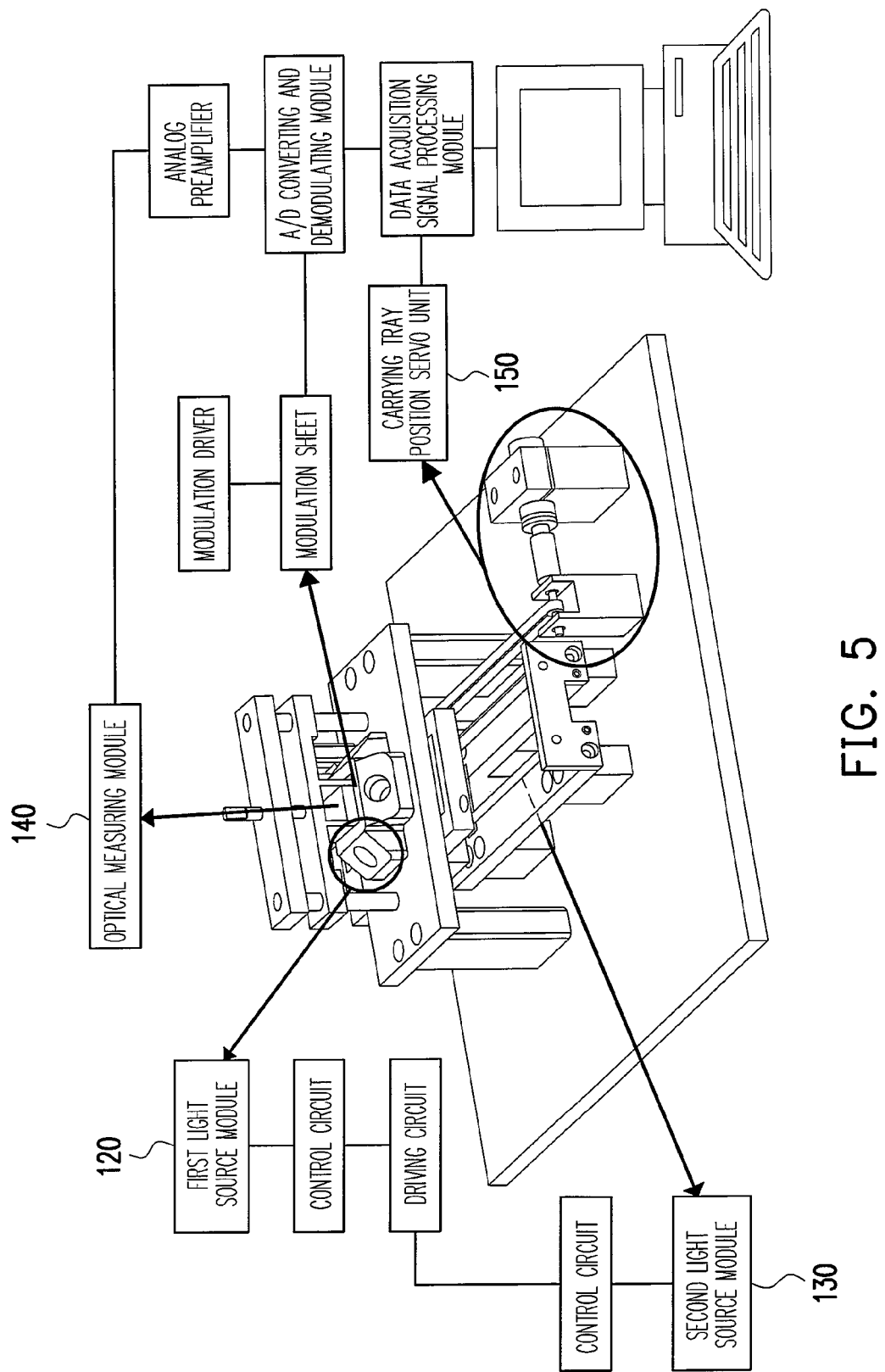
FIG. 5 is a view showing a measuring architecture of optical phase-locking amplifying.

By using modulation or demodulation method within the architecture of optical phase-locking amplification, the sensitivity of measuring signal is largely improved. FIG. 5 is a view showing a measuring architecture of optical phase-locking amplification. Referring to FIG. 5, the light emitted by the first light source module 120 passes through the modification sheet of the first optical modulation unit 122 and is converted into a modulated light beam to irradiate a specimen 111. An optical measuring module 140 senses the optical signal and outputs the sensed signal. The sensed signal is sent to an analog preamplifier and then demodulated by a demodulation circuit and converted into a digital signal by an analog-to-digital converter. The digital signal enters a computer or an embedded system for processing via a data acquisition card, wherein the analog preamplifier can be a logarithmic amplifier module to provide high-sensitivity and high-dynamic range optical measurement.

The optical measuring system 100 further includes a carrying tray position servo unit 150, which includes a linear driving motor 152 and a linear transmission mechanism 154. A carrying tray 11 is fixed on the linear driving mechanism 154 and the linear transmission mechanism 154 is connected to the linear driving motor 152. The carrying tray 110 takes an attachable design to assemble with the linear transmission mechanism 154, which provides a convenience to load or replace a specimen. The carrying tray position servo unit 150 can adjust the specimen position so as to place the specimen accurately within the probing range of the optical measuring module 140.

The above-mentioned carrying tray position servo unit 150 can be implemented by using any appropriate technique. In the following, a direct current motor (DC motor) is exemplarily used to implement the linear driving motor 152. The commonly used position encoder by a DC motor is, for example, photo encoder or Hall encoder, all of which are required for operation and processing near to the rotation axis of the motor so as to make the position encoder work regularly. However, instead of the above-mentioned encoders, a commutating encoder is employed herein, which exempts additional processing near to the motor but is able to achieve the position-tracking goal as well.

The operation principle of a DC motor rests in two brushes that are disposed at two outer ends of the commutator and the brushes are fed by a direct current, so as to generate two magnetic fields with a push-pull action force (or a moment) causing a rotation action. The rotation further makes the commutator produce an electrical commutation so as to form a moment with a fixed turning direction for continuous rotation. In fact, the transformation phenomena include alternately switching operations between a virtual short circuit between the brushes at the outer ends and several sets of windings and turning on the windings. From the point of view of a transformer's primary side, the commutating works just like a load at the secondary side to be switched between two levels.

Figure 2A:
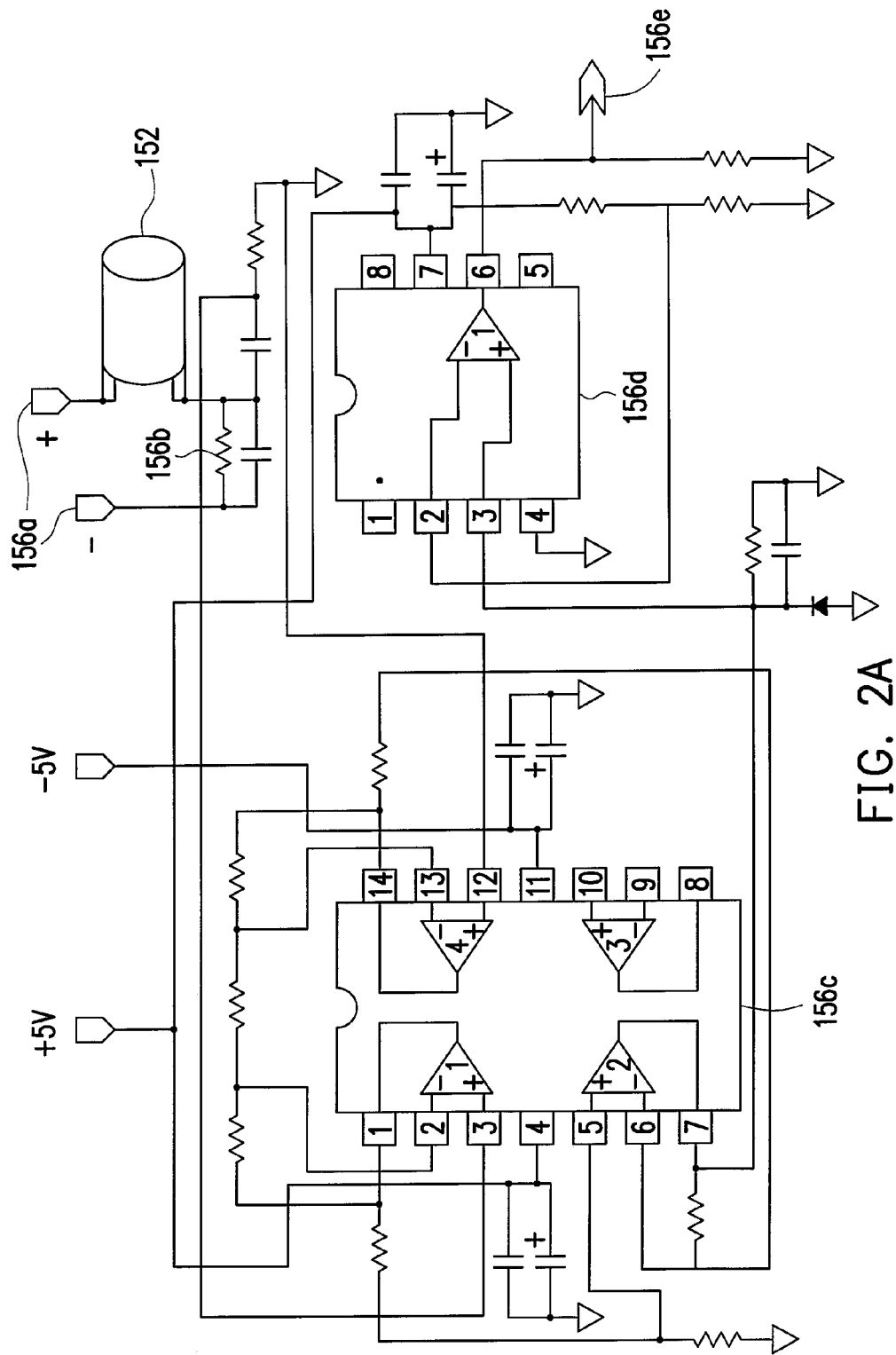
FIG. 2A is a schematic circuit diagram of a commutating encoder.
Figure 2B:
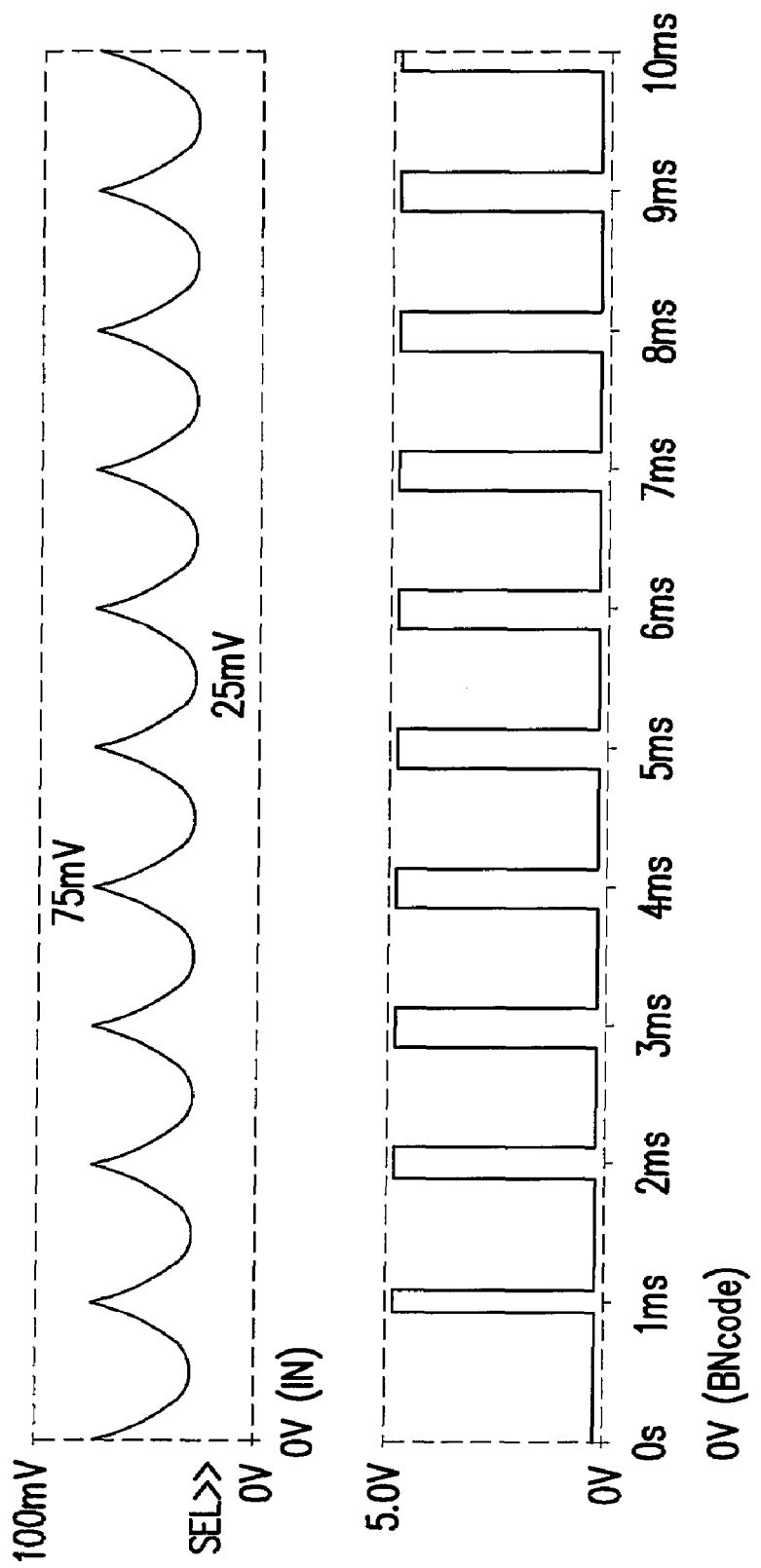
FIG. 2B is a diagram showing pulses and encoded pulses generated by a commutator.

FIG. 2A is a schematic circuit diagram of a commutating encoder. Referring to FIG. 2A, a current-sensing resistor 156b is serially connected to an electrically live loop containing a motor-driving circuit 156a and the linear driving motor 152, wherein the current-sensing resistor 156b is employed for measuring pulse signal generated by the commutator. Then, the sensed pulse signal generated by the commutator is sent to a differential amplifier 156c and a pulse shaping circuit 156d for processing and an encoding output terminal 156e outputs an encoded pulse signal. The pulse number generated by the commutator for one turn is twice as large as the number of winding sets. Thus, the turn number of the commutator can be derived from the pulse number, and the position of the carrying tray may be obtained. FIG. 2B is a diagram showing pulses and encoded pulses generated by a commutator. Referring to FIG. 2B, the upper graph thereof shows the pulses generated by the commutator. After the pulses are processed by the differential amplifier 156c and the pulse shaping circuit 156d, an encoded pulse signal is obtained and shown by the lower graph in FIG. 2B.

Figure 3:
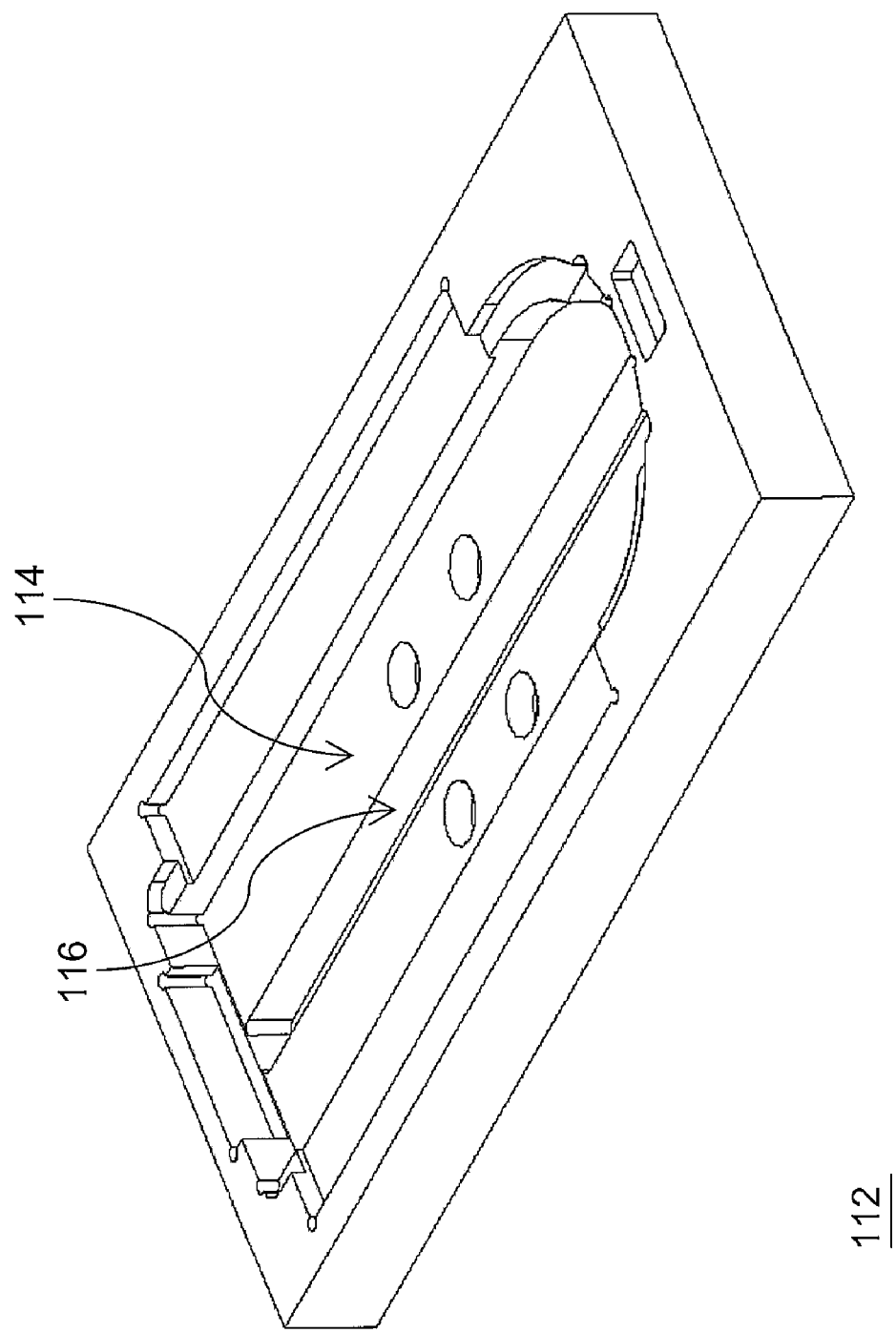
FIG. 3 is a view of the carrying vessel in FIG. 1.

FIG. 3 is an implementation diagram of the specimen-fixing mechanism in FIG. 1. Referring to FIGS. 1B and 3, a carrying tray 110 includes a specimen-fixing mechanism, which is implemented by a carrying vessel 112 in an embodiment of the present invention. However, anyone skilled in the art may modify the design to fix a specimen. A cavity 114 or a plurality of cavities 114 with different depths and different widths are made on the carrying vessel 112 for placing specimens in different sizes. The bottom of the cavity 114 has multiple hollow cavities 116, which enable the light emitted by the second light source module 130 to be struck onto the specimen (not shown) for conducting transmittive optical measurement.

Figure 4A:
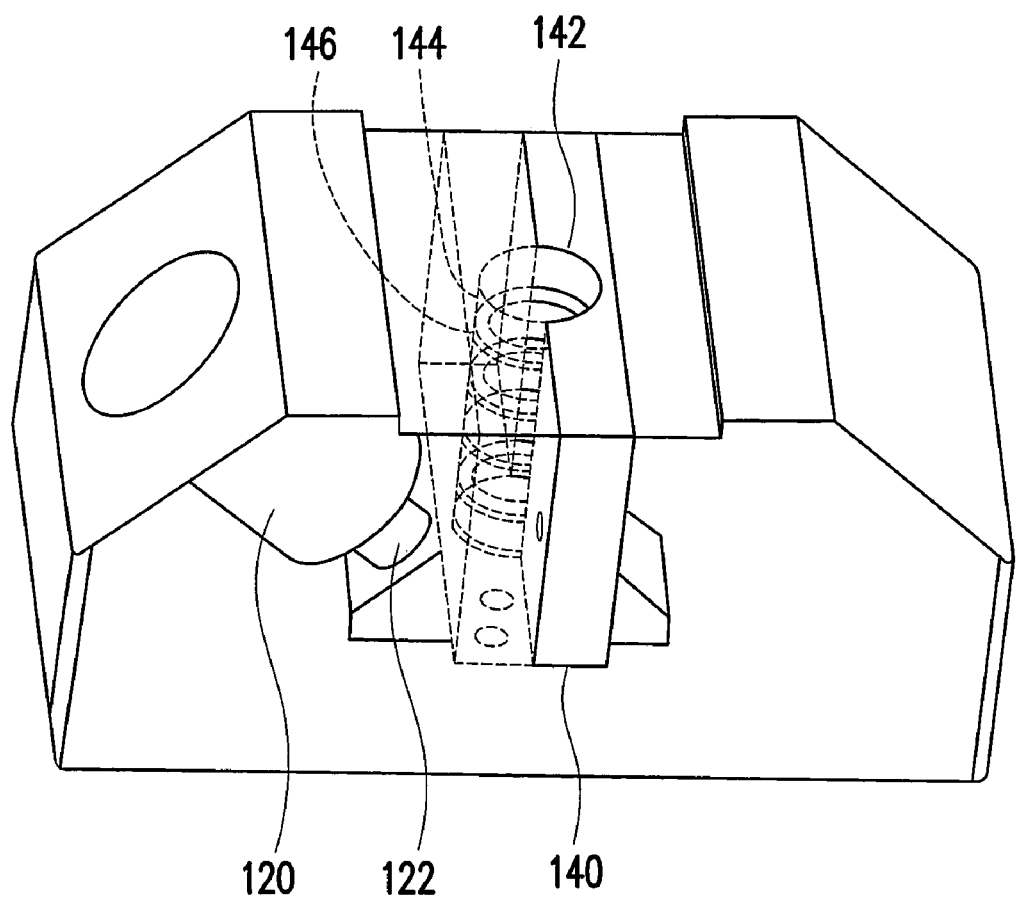
FIG. 4A is a wire-frame view of the optical measuring module in FIG. 1.
Figure 4B:
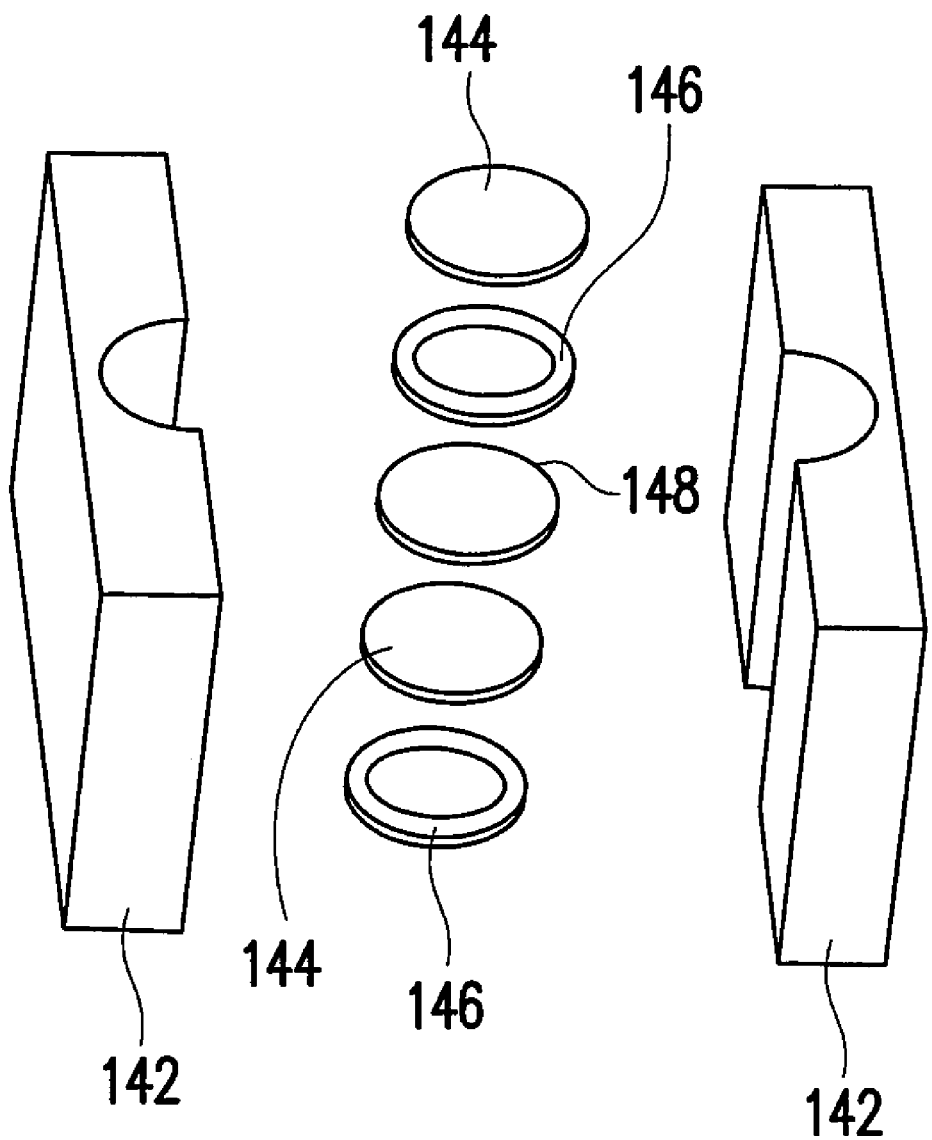
FIG. 4B is an exploded view of the optical measuring module in FIG. 1.

FIG. 4A is a wire-frame view of the optical measuring module 140 in FIG. 1B, FIG. 4B is an exploded view of the optical measuring module 140 in FIG. 1, and these views are not plotted according the real dimensions thereof. Referring to FIGS. 4A and 4B, an optical measuring module 140 includes a carrying barrel 142. The carrying barrel 142 has at least a lens 144 and at least a washer 146 disposed therein. An optical filter 148 is disposed between the lenses. The washer 146 is employed for adjusting the positions of the lens 144 and the optical filter 148 in the carrying barrel 142. Although commercially available lenses may have a same focal length, but the sizes and thicknesses thereof may not be the same. Therefore, the washer 146 is used to adjust the lens positions. In particular, while conducting different experiments, it is convenient to adjust the lens positions by adjusting the washer 146 to meet the requirement of substituting the lenses of different focal lengths. Thus, the standard lenses available in the market may be utilized so that no specially designed lenses are required. The optical measuring module 140 in an embodiment of the present invention employs two lenses, an optical filter and two washers. However, anyone skilled in the art may also apply the present invention in, for example, a confocal microscope testing system.

In a confocal microscope testing system, the focus position of object lens and focus position of imaging lens (convergence lens) of the microscope are symmetrical to each other; that is, in terms of optical imaging, the illumination point and the probing point are conjugated, and the focuses of the above-mentioned two lenses are simultaneously located on the surface of the observed sample. The confocal microscope has a unique pin-hole disposed in front of a detector to perform special filtering, which makes the confocal microscope have an optical slicing capability which the conventional optical microscope does not have. The working principle of a confocal microscope is that when a light beam is focused at somewhere of a sample instead on the focus plane, most of the reflected light beam from the sample fail to pass through the pin-hole in front of the optical detector so as to fail imaging; in contrast, an extreme intensive optical signal is produced and the imaging principle of a confocal microscope is based on Fourier optics. Due to the disposed pin-hole and the special filtering the pin-hole performs, although the lateral resolution of the confocal microscope has only a little improvement than a conventional microscope, but the longitudinal resolution thereof is much greater than the conventional one. Usually, an optical spot produced by a confocal microscope is less than that produced by a conventional microscope. Therefore, the confocal microscope has higher plane resolution and more excellent sectioning capability than the conventional microscope. In practice however, the confocal imaging is often limited by absorption and dispersion of a sample so that the penetrating depth and the signal-to-noise ratio are largely affected.

The optical measuring system 100 further includes an optical measuring position servo unit (not shown), a position servo unit of first light source module (not shown), a position servo unit of second light source module (not shown) and a detection circuit (not shown).

Referring to FIG. 1B, the optical measuring position servo unit (not shown) is for adjusting the distance between the optical measuring module 140 and the carrying tray 110 to allocate a specimen located within the probing range of the optical measuring module 140.

The position servo unit of first light source module (not shown) is for adjusting the distance between the first light source module 120 and the carrying tray 110 so as to allocate the specimen (not shown) on the optical path of the first light source module 120.

The position servo unit of second light source module (not shown) is for adjusting the distance between the second light source module 130 and the carrying tray 110 so as to allocate the specimen (not shown) located on the optical path of the second light source module 130.

The detection circuit (not shown) is electrically connected to the optical measuring module 140 for detecting the measurement result of the optical measuring module 140. The detection circuit includes a logarithmic amplifier (not shown) to enable the optical measuring system to conduct high-sensitivity and high-dynamic range optical measurement.

A logarithmic amplifier is an amplifying circuit where the amplitude of output signal and the amplitude of input signal have a logarithmic function relationship therebetween. A real logarithmic amplifier always has both linear and logarithmic amplification functions. When an input signal is weak, the logarithmic amplifier functions as a linear amplifier; for a larger gain and when an input signal gets strong, the amplifier functions as a logarithmic amplifier, wherein the gain thereof is decreased with an increasing input signal. In the present invention, since the dynamic range of the input signal is usually quite broad and the amplitude of an optical signal is extremely weak, thus, a logarithmic amplifier can be used to meet the requirement of the present invention, where a weak signal may be amplified to a high gain, a strong signal would automatically lower the gain so as to avoid saturation. The major performance of a logarithmic amplifier is often represented by input dynamic range Din and output dynamic range Dout:

$$D_{in} = 20 \, \text{Log}(U_{1H}/U_{1L}) \, (\text{dB}) \tag{1}$$

$$D_{out} = 20 \, \text{Log}(U_{2H}/U_{2L}) \, (\text{dB}) \tag{2}$$

$U_{1L}$ and $U_{1H}$ in the above-mentioned formulas are respectively an input voltage corresponding to an amplification characteristic covering from linear relation to logarithmic relationship and an input voltage corresponding to the saturation status; and $U_{2L}$ and $U_{2H}$ correspond to output voltages. A properly designed logarithmic amplifier can reach and beyond 100 dB of input signal dynamic range, but less than 30 dB of output signal dynamic range. For example, assuming a specimen requires a 100 pg/ml high sensitivity and a 100 pg/ml-0.01 μg/ml high dynamic range, in terms of dynamic range of concentration (for preliminary estimation), the corresponding input signal dynamic range may be calculated by:

$$D_{in}=20 \, Log(10^{-8}/10^{-10})=40(dB) \quad (3)$$

For a commercially available logarithmic amplifier today, the achievable input signal dynamic range is 100 dB. In addition to dynamic range, the performance index of a logarithmic amplifier also includes accuracy of logarithmic relation and frequency response. The voltage across a diode PN-junction is a logarithmic function of the PN-junction current. Thus, a diode is often used as a load or a feedback component of an amplifier to make the amplifier have logarithmic amplitude characteristic. Although an amplifier employing diodes is advantageous in simpler circuit, however, the achievable input dynamic range is usually less than 50 dB only. Besides, the bandwidth of the amplifier using diodes is limited by the PN-junction capacitance. In industrial practice, multi-stages of amplifiers connected in series or parallel are adopted to result in an approximate logarithmic amplification characteristic and have good effect. A practical logarithmic amplifier usually employs 4-10 stages of amplitude-limiting amplifiers. When the dynamic range of an amplifier is specified, more stages are helpful to achieve a more accurate logarithmic relationship. The above-mentioned detection circuit can be implemented referring to FIG. 5.

Referring to FIG. 1B, the specimen (not shown) is placed at the first side of the carrying tray 110 and located on the optical path of the first light source module 120. The first light source module 120 emits a light onto the specimen so that the optical measuring module 140 is able to conduct a reflective optical measurement including fluorescence radiation measurement on the specimen.

Taking a fluorescence radiation measurement as example, note that biometric tissue itself usually contains fluorescence molecules, which can be stimulated by double-photons. Some useful high energy molecules in biometric tissue, for example, nicotinamide adenine dinucleotide phosphate (NADPH) and nicotinamide adenine dinucleotide (NADH), produce fluorescence. The absorption spectrum line of independent NADPH or NADH is 340 nm while emitting 460 nm fluorescence. An area with high metabolism rate has higher image luminance due to the high concentration of NADPH or NADH in the area. Therefore, NADPH fluorescence or NADH fluorescence can be used for monitoring redox state in cornea and skin.

The specimen (not shown) is placed on the carrying tray 110 and located on the optical path of the second light source module 130. The second light source module 130 emits a light onto the specimen so that the optical measuring module 140 conducts a transmittive optical measurement including Laman spectrum measurement on the specimen.

Taking optical absorption measurement as an example, note that optical absorption measurement is applicable to substance having a specific absorption spectrum. For example, DNA has a maximum absorption value in response to 260 nm ultraviolet light, and single-strand DNA and double-strand DNA have different absorption values. Thus, by using the absorption value of solution in response to 260 nm ultraviolet light, the content proportion of single-strand DNA over double-strand DNA in the solution can be obtained.

In biochemical analysis, coefficient of variation index (CVI) is equal to within-laboratory standard deviation divided by within-group standard deviation, that is a matching parameter between the within-laboratory standard deviation and that of all the laboratories using the same method. In this way, a whole analysis process can be distinguished or a specific instrument can be evaluated for the accuracy thereof.

Figure 6:
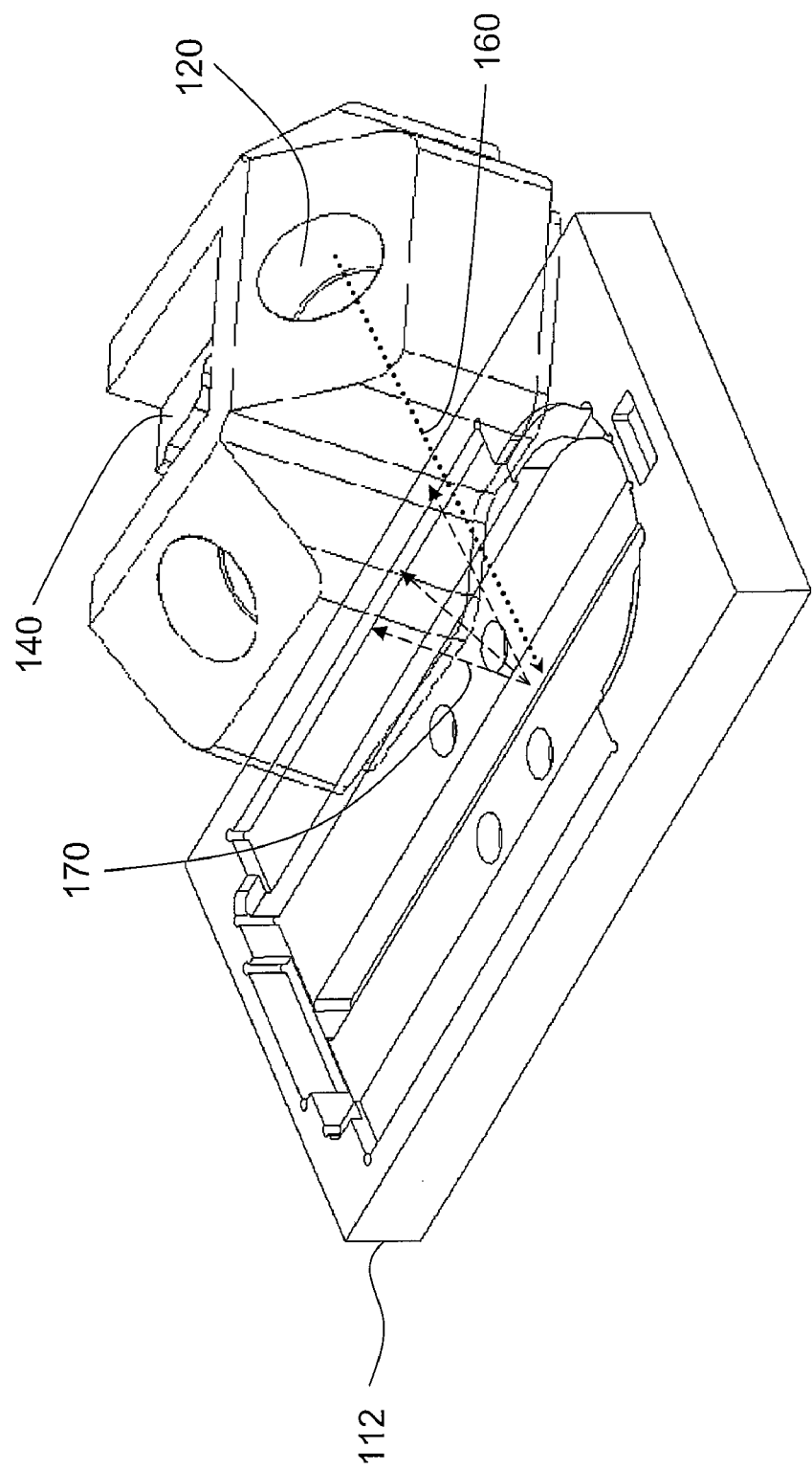
FIG. 6 is a view of the measuring architecture according to an embodiment of the present invention.
Figure 7A:
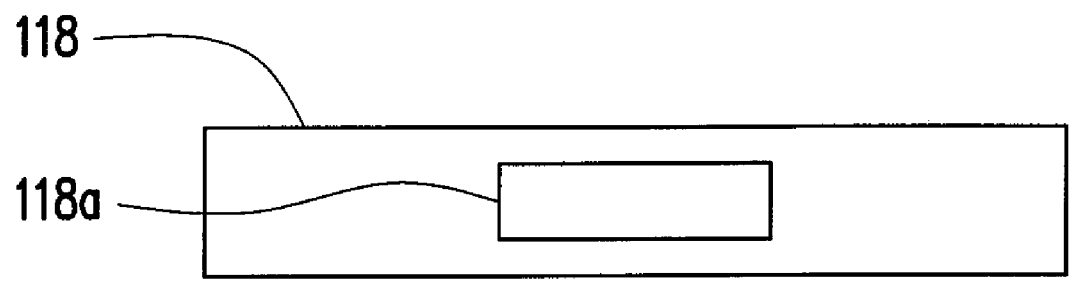
FIG. 7A is a view of disposition of the substance to be tested.

FIG. 6 is a view of the measuring architecture according to an embodiment of the present invention. FIG. 7A is a view of disposition of the substance to be tested in FIG. 6. Referring to FIGS. 6 and 7A, the first light source module 120 emits a light 160 onto the carrying sheet 118 and the optical measuring module 140 measures the reaction light 170 of substance to be tested 118a.

Figure 8A:
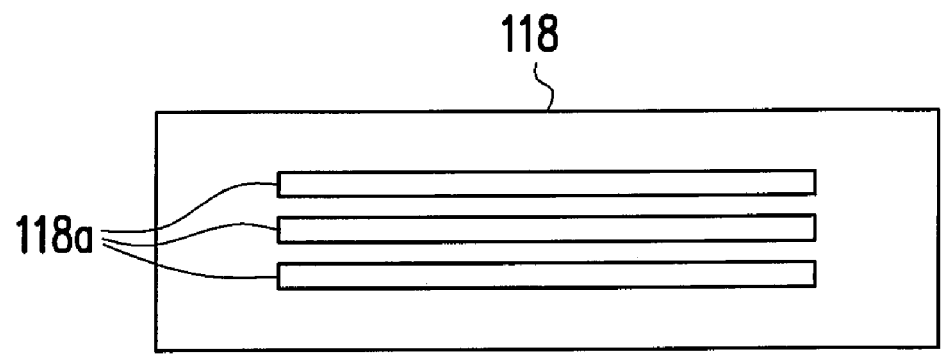
FIG. 8A is another diagram of disposition of the substance to be tested.
Figure 9A:
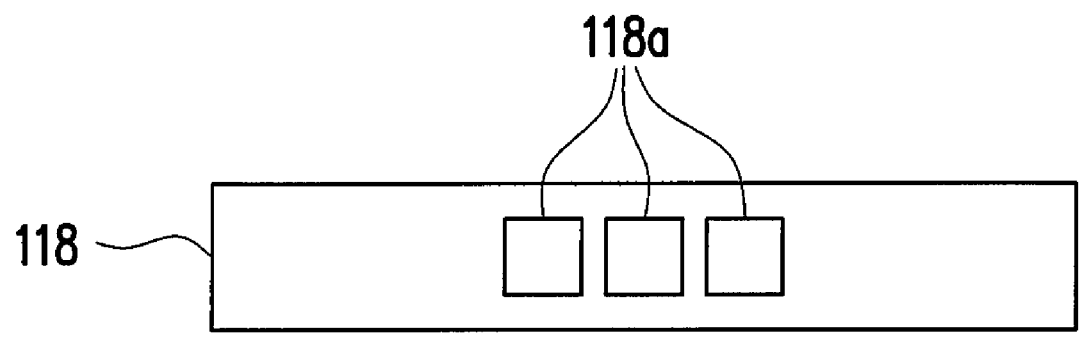
FIG. 9A is another diagram of spread substance to be tested in FIG. 6.

FIG. 8A is a view of disposition of the substance to be tested in FIG. 6 according another embodiment of the present invention, and FIG. 9A is a view of disposition of the substance to be tested in FIG. 6 according to yet another embodiment of the present invention. Referring to FIGS. 7A, 8A and 9A, a block of substance to be tested can be changed from an original large region (as shown by FIG. 7A) into three smaller regions (as shown by FIG. 8A or 9A).

Figure 7B:
FIG. 7B is a measured signal diagram corresponding to FIG. 7A.
Figure 8B:
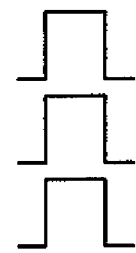
FIG. 8B is a measured signal diagram corresponding to FIG. 8A.
Figure 8C:
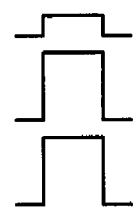
FIG. 8C is another measured signal diagram corresponding to FIG. 8A.
Figure 9B:
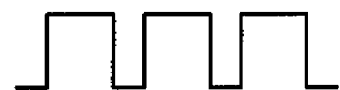
FIG. 9B a measured signal diagram corresponding to FIG. 9A
Figure 9C:
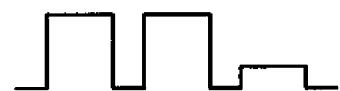
FIG. 9C is another measured signal diagram corresponding to FIG. 9A

FIG. 7B is a measured signal diagram corresponding to FIG. 7A, FIG. 8B is a measured signal diagram corresponding to FIG. 8A, FIG. 8C is another measured signal diagram corresponding to FIG. 8A, FIG. 9B a measured signal diagram corresponding to FIG. 9A and FIG. 9C is another measured signal diagram corresponding to FIG. 9A. Referring to FIGS. 7B, 8B, 8C, 9B and 9C, during a set of measurements, the spreading scheme of FIG. 7A only produces a measuring signal (as shown by FIG. 7B), but the spreading schemes of FIGS. 8A and 9A can produce three measuring signals (as shown by FIGS. 8B and 9B), wherein among three measured light luminance values corresponding to the three regions, if the quotient of the largest value divided by the smallest value keeps under a certain proportion, the coefficients of variation (CV) of the three values are evaluated by the instrument, and the average value of two measured values with less CV than that of the third value is selected as the measured result value of the set of measurements (as shown by FIGS. 8C and 9C). The three regions can be arranged in parallel, while an array-type optical measuring head conducts measurement, as shown by FIG. 8A; however, the three regions can also be arranged in series, as shown by FIG. 9A.

The above-mentioned scheme of dividing a spreading block of substance to be tested into three regions has an advantage that when a specimen measuring result is judged as void due to partial pollution of a chip or disabled reactant (for example, disabled fluorescent substance), it is not necessarily to measure all over again.

In summary, the present invention uses two light source modules to respectively conduct a reflective optical measurement and a transmittive optical measurement so as to achieve the goal of different optical measurement on a same assay table. Thus, time for transferring specimen between different measurement assay tables may be saved and the quantity of specimen for testing may be substantially reduced.

In addition, the optical measuring module of the system provided by the present invention has adjustable flexible design, which includes the optical components that are commercially available in the market. Therefore no specially designed optical components are required, and thus the practical applicability is increased and the cost is reduced.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An optical measuring system, comprising:
   a carrying tray, for carrying a specimen comprising a carrying sheet, wherein the carrying sheet is divided into multiple regions for distribution of substance to be tested;
   a first light source module, disposed at a first side of the carrying tray, wherein the specimen is located on the optical path of the first light source module;
   a second light source module, disposed at a second side of the carrying tray, wherein the specimen is located on the optical path of the second light source module; and
   an optical measuring module, disposed at the first side or the second side of the carrying tray, conducting photometry on each of the regions, comparing the results thereof, and calculating an average value for two regions with less coefficient of variation (CV) as a measurement value according to the comparison results, wherein the specimen is located within a probing range of the optical measuring module.

2. The optical measuring system according to claim 1, wherein the first side and the second side of the carrying tray are respectively an upper side and a lower side of the carrying tray.

3. The optical measuring system according to claim 1, wherein the specimen is disposed at the first side of the carrying tray.

4. The optical measuring system according to claim 1, wherein the specimen is disposed at the second side of the carrying tray.

5. The optical measuring system according to claim 1, further comprising:
   a carrying tray position servo unit, connected to the carrying tray, for adjusting the position of the carrying tray to allocate the specimen within the probing range of the optical measuring module.

6. The optical measuring system according to claim 1, wherein the carrying tray position servo unit comprises:
   a linear driving motor; and
   a linear transmission mechanism for connecting the linear driving motor with the carrying tray.

7. The optical measuring system according to claim 1, wherein the carrying tray comprises a specimen-fixing mechanism for fixing the specimen onto the carrying tray.

8. The optical measuring system according to claim 7, wherein the specimen-fixing mechanism comprises a carrying vessel having at least a cavity for carrying the specimen.

9. The optical measuring system according to claim 8, wherein at least a hollow cavity is disposed on the bottom of the cavity.

10. The optical measuring system according to claim 7, wherein the specimen-fixing mechanism comprises a carrying vessel having a plurality of cavities with different depths and different widths for carrying specimens of different sizes.

11. The optical measuring system according to claim 1, wherein the specimen comprises a flat biochip.

12. The optical measuring system according to claim 1, wherein the specimen comprises an optical fiber chip.

13. The optical measuring system according to claim 12, wherein the optical fiber chip comprises a coupling-type optical fiber chip.

14. The optical measuring system according to claim 1, wherein the wavelength of a light emitted by the first light source module is different from that emitted by the second light source module.

15. The optical measuring system according to claim 1, wherein the wavelength of a light emitted by the first light source module is same as that emitted by the second light source module.

16. The optical measuring system according to claim 1, wherein the first light source module emits a monochromatic light.

17. The optical measuring system according to claim 1, wherein the first light source module emits a multi-chromatic light.

18. The optical measuring system according to claim 1, wherein the second light source module emits a monochromatic light.

19. The optical measuring system according to claim 1, wherein the second light source module emits a multi-chromatic light.

20. The optical measuring system according to claim 1, wherein the optical measuring module is disposed at the first side of the carrying tray.

21. The optical measuring system according to claim 1, wherein the optical measuring module is comprised of an array-type optical measuring module.

22. The optical measuring system according to claim 20, wherein the first light source module is used to conduct a reflective optical measurement on the specimen.

23. The optical measuring system according to claim 20, wherein the first light source module is employed to conduct a fluorescent radiation measurement on the specimen.

24. The optical measuring system according to claim 20, wherein the second light source module is employed to conduct a transmittive optical measurement on the specimen.

25. The optical measuring system according to claim 20, wherein the second light source module is employed to conduct a Laman spectrum measurement on the specimen.

26. The optical measuring system according to claim 20, wherein the second light source module is employed to conduct an optical absorption measurement on the specimen.

27. The optical measuring system according to claim 1, wherein the optical measuring module comprises:
   a carrying barrel;
   at least a lens, disposed in the carrying barrel; and
   at least a washer, disposed in the carrying barrel for adjusting a position of the lens in the carrying barrel.

28. The optical measuring system according to claim 1, further comprising an optical measuring position servo unit, for adjusting a distance between the optical measuring module and the carrying tray so as to allocate the specimen within the probing range of the optical measuring module.

29. The optical measuring system according to claim 1, further comprising:
   a position servo unit of first light source module, for adjusting a distance between the first light source module and the carrying tray; so as to allocate the specimen on the optical path of the first light source module.

30. The optical measuring system according to claim 1, further comprising:
   a position servo unit of second light source module, for adjusting a distance between the second light source module and the carrying tray so as to allocate the specimen on the optical path of the second light source module.

31. The optical measuring system according to claim 1, wherein the first light source module further comprises a first optical modulation unit for modulating a light emitted by the first light source module.

32. The optical measuring system according to claim 31, wherein the first optical modulation unit comprises a modification sheet for intermittently blocking the optical path of the first light source module so as to enable the optical measuring system to perform high-sensitivity phase-locking optical measurement.

33. The optical measuring system according to claim 1, wherein the second light source module comprises a second optical modulation unit for modulating a light emitted by the second light source module.

34. The optical measuring system according to claim 33, wherein the second optical modulation unit comprises a modification sheet for intermittently blocking the optical path of the second light source module so as to enable the optical measuring system to perform high-sensitivity phase-locking optical measurement.

35. The optical measuring system according to claim 1, further comprising a detection circuit electrically connected to the optical measuring module for detecting the measuring results of the optical measuring module.

36. The optical measuring system according to claim 35, wherein the detection circuit comprises a logarithmic amplifier for logarithmically amplifying the measuring results of the optical measuring module so as to enable the optical measuring system to perform high-sensitivity phase-locking optical measurement.

37. The optical measuring system according to claim 1, wherein the regions are arranged along a longitudinal direction of the carrying sheet.

38. The optical measuring system according to claim 1, wherein the regions are arranged along a direction perpendicular relative to the longitudinal direction of the carrying sheet.

* * * * *